US012622588B2

(12) United States Patent <br> Annecchino et al.

(10) Patent No.: US 12,622,588 B2 <br> (45) Date of Patent: May 12, 2026

(54) SYSTEMS AND METHODS FOR SCS THERAPY OPTIMIZATION

(71) Applicant: Boston Scientific Neuromodulation Corporation, Valencia, CA (US)

(72) Inventors: Luca Antonello Annecchino, London (GB); Matthew Lee McDonald, Glendale, CA (US); Que T. Doan, West Hills, CA (US); Changfang Zhu, Valencia, CA (US); Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 761 days.

(21) Appl. No.: 17/988,609

(22) Filed: Nov. 16, 2022

(65) Prior Publication Data

US 2023/0148877 A1 May 18, 2023

Related U.S. Application Data

(60) Provisional application No. 63/280,215, filed on Nov. 17, 2021.

(51) Int. Cl.
| | |
|---|---|
| *A61B 5/0205* | (2006.01) |
| *A61B 5/00* | (2006.01) |
| *A61B 5/024* | (2006.01) |

(52) U.S. Cl.
CPC ............ *A61B 5/0205* (2013.01); *A61B 5/024* (2013.01); *A61B 5/74* (2013.01)

(58) Field of Classification Search
CPC .......... A61B 5/0205; A61B 5/024; A61B 5/74
See application file for complete search history.

(56) References Cited

U.S. PATENT DOCUMENTS

| | | |
|---|---|---|
| 8,103,351 B2 | 1/2012 | Rondoni et al. |
| 10,471,264 B2 | 11/2019 | Bourget et al. |
| | (Continued) | |

FOREIGN PATENT DOCUMENTS

| | | |
|---|---|---|
| EP | 4433151 | 6/2025 |
| WO | 2021003290 | 1/2021 |
| | (Continued) | |

OTHER PUBLICATIONS

"International Application Serial No. PCT US2022 050140, International Search Report mailed Feb. 24, 2023", 5 pgs.

(Continued)

*Primary Examiner* — William J Levicky <br> *Assistant Examiner* — Jessandra F Hough <br> (74) *Attorney, Agent, or Firm* — Schwegman Lundberg & Woessner, P.A.

(57) ABSTRACT

A system may include a neuromodulator and a processing system. The neuromodulator may be configured to be programmed with a set of more than one program to deliver neuromodulation. The processing system may be configured to: receive sensed data indicative of activity, motion and/or posture of a patient; analyze the activity, motion and/or posture of the patient; and perform a process, based on the analyzed activity, motion and/or posture, for switching from one program in the set of more than one program to another program from the set of more than one program. The process may include automatically implementing the other program from the set of more than one program or suggesting to switch to the other program from the set of more than one program.

20 Claims, 11 Drawing Sheets

(56)                 References Cited

U.S. PATENT DOCUMENTS

| | | | |
|---|---|---|---|
| 10,576,282 | B2 | 3/2020 | Doan et al. |
| 10,610,688 | B2 | 4/2020 | Thakur et al. |
| 10,631,777 | B2 | 4/2020 | Clark et al. |
| 2004/0019370 | A1* | 1/2004 | Gliner ................ A61N 1/36017 |
| | | | 607/48 |
| 2008/0281381 | A1 | 11/2008 | Gerber et al. |
| 2009/0299432 | A1* | 12/2009 | Stadler ............... A61N 1/36521 |
| | | | 607/28 |
| 2011/0172743 | A1* | 7/2011 | Davis ................ A61N 1/36535 |
| | | | 340/573.7 |
| 2014/0005755 | A1* | 1/2014 | Wolf, II ............... A61B 5/1116 |
| | | | 607/88 |
| 2015/0127062 | A1* | 5/2015 | Holley ............... A61N 1/37247 |
| | | | 607/46 |
| 2016/0166326 | A1 | 6/2016 | Bakker et al. |
| 2017/0282360 | A1* | 10/2017 | Telleria ..................... F16J 3/04 |
| 2019/0022397 | A1* | 1/2019 | Srivastava ......... A61N 1/36139 |
| 2019/0184167 | A1* | 6/2019 | Vansickle .......... A61N 1/36185 |
| 2019/0209844 | A1* | 7/2019 | Esteller ............. A61N 1/36071 |
| 2019/0358455 | A1* | 11/2019 | Lin .................... A61N 1/36139 |
| 2020/0009367 | A1 | 1/2020 | Huertas Fernandez et al. |
| 2020/0009386 | A1* | 1/2020 | Mansell ............... A61N 1/3615 |
| 2020/0009394 | A1 | 1/2020 | Huertas Fernandez et al. |
| 2020/0046980 | A1 | 2/2020 | Moffitt et al. |
| 2020/0147388 | A1 | 5/2020 | Huertas Fernandez et al. |
| 2020/0147390 | A1 | 5/2020 | Zhang et al. |
| 2020/0147391 | A1 | 5/2020 | Moffitt |
| 2020/0147392 | A1 | 5/2020 | Doan et al. |
| 2020/0147393 | A1 | 5/2020 | Zhang et al. |
| 2020/0147397 | A1 | 5/2020 | Huertas Fernandez et al. |
| 2020/0147400 | A1 | 5/2020 | Moffitt et al. |
| 2020/0254256 | A1 | 8/2020 | Moffitt et al. |
| 2020/0353256 | A1* | 11/2020 | Vallejo ............... A61N 1/36071 |
| 2021/0299448 | A1 | 9/2021 | Doan et al. |

FOREIGN PATENT DOCUMENTS

| | | |
|---|---|---|
| WO | 2021016867 | 2/2021 |
| WO | 2021126433 | 6/2021 |
| WO | 2021141652 | 7/2021 |
| WO | 2021158310 | 8/2021 |
| WO | 2021178105 | 9/2021 |
| WO | 2023091510 | 5/2023 |

OTHER PUBLICATIONS

"International Application Serial No. PCT US2022 050140, Written Opinion mailed Feb. 24, 2023", 6 pgs.
"International Application Serial No. PCT US2022 050140, International Preliminary Report on Patentability mailed May 30, 2024", 8 pgs.
"European Application Serial No. 22826523.7, Response to Communication Pursuant to Rules 161 and 162 filed Dec. 17, 2024", 14 pgs.
"Australian Application Serial No. 2022392201, First Examination Report mailed Mar. 28, 2025", 3 pgs.
"Australian Application Serial No. 2022392201, Response filed Sep. 26, 2025 to First Examination Report mailed Mar. 28, 2025", 15 pgs.

* cited by examiner

833

MEASURE IMPEDANCE
[AND/OR ECAP]

834

IF IMPEDANCE [AND/OR ECAP] CHANGES
IN EXCESS OF VARIABILITY TOLERANCE
($\Delta Z_{th}$ OR $\Delta ECAP_{th}$)
AND
FOR LONGER THAN DURATION TOLERANCE
($\Delta t_{th}$)

835

THEN CHANGE SCS SETTINGS
AND/OR
TRIGGER QUESTIONNAIRE

INDUCED BY BODY MOTION

IMPEDANCE $Z_0$ $\Delta Z > \Delta Z_{th}$

936

TIME

937

SYSTEMS AND METHODS FOR SCS THERAPY OPTIMIZATION

CLAIM OF PRIORITY

This application claims the benefit of U.S. Provisional Application No. 63/280,215, filed on Nov. 17, 2021, which is hereby incorporated by reference in its entirety.

TECHNICAL FIELD

This document relates generally to medical systems, and more particularly, but not by way of limitation, to systems, devices, and methods for determining or optimizing Spinal Cord Stimulation (SCS) therapy.

BACKGROUND

Neuromodulation, also referred to as neurostimulation, has been proposed as a therapy for a number of conditions. Examples include Spinal Cord Stimulation (SCS), Deep Brain Stimulation (DBS), Peripheral Nerve Stimulation (PNS), and Functional Electrical Stimulation (FES).

Implantable neuromodulation systems have been applied to deliver SCS therapy. An implantable neuromodulation system may include an implantable neuromodulator, which may also referred to as an implantable pulse generator (IPG), and one or more implantable leads each including one or more electrodes. The implantable neuromodulator delivers neuromodulation energy through one or more electrodes placed on or near a target site in the nervous system.

An external programming device is commonly used to program the implantable neurostimulator with stimulation parameters controlling the delivery of the neurostimulation energy. Modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). The values for these parameters may be customized to a patient. The modulation parameters may be configured as a neuromodulation program capable of being implemented by the neuromodulator, and the neurostimulator may be programmed with more than one program. In order to find a program that provides an effectively provides a therapy (e.g., pain relief) with negligible side effects, the patient or clinician may implement different programs within the neuromodulator. However, further optimization of the SCS therapy for the patient is desirable.

SUMMARY

An example (e.g., "Example 1") of a system may include a neuromodulator and a processing system. The neuromodulator may be configured to be programmed with a set of more than one program to deliver neuromodulation. The processing system may be configured to: receive sensed data indicative of activity, motion and/or posture of a patient; analyze the activity, motion and/or posture of the patient; and perform a process, based on the analyzed activity, motion and/or posture, for switching from one program in the set of more than one program to another program from the set of more than one program. The process may include automatically implementing the other program from the set of more than one program or suggesting to switch to the other program from the set of more than one program.

In Example 2, the subject matter of Example 1 may optionally be configured such that the system includes at least one of a wearable device, a mobile electronic device, or a remote control, and the processing system includes at least one processor in at least one of the wearable device, the mobile electronic device or the remote control. By way of example and not limitation, a wearable device may include a watch, and a mobile electronic device may include a phone, a tablet or pad. The processing system may be located in a single device or distributed over more than one device such that some processing is performed in different local devices.

In Example 3, the subject matter of any one or more of Examples 1-2 may optionally be configured to include a watch or a phone configured to determine the activity, motion and/or posture of the patient.

In Example 4, the subject matter of any one or more of Examples 1-3 may optionally be configured such that the neuromodulator is configured to deliver neuromodulation using one or more electrodes on a lead, the system further comprising an accelerometer or gyroscope inside of a tip or a body of the lead, wherein the accelerometer or gyroscope is configured for use to provide at least some of the sensed data indicative of the activity, motion and/or posture of the patient.

In Example 5, the subject matter of any one or more of Examples 1-4 may optionally be configured to include a strain or flex sensor in an implanted lead, where the strain or flex sensor is configured to detect lead curvature, wherein the implanted lead is implanted along a spine such that the lead curvature is indicative of spine curvature, and the system is configured to use the strain or flex sensor to determine at least some of the sensed data indicative of the activity, motion and/or posture of the patient.

In Example 6, the subject matter of Example 5 may optionally be configured such that the strain or flex sensor includes a fiber optic bending sensor.

In Example 7, the subject matter of any one or more of Examples 1-6 may optionally be configured such that the sensed data indicative of activity, motion and/or posture includes sensed data for at least one of posture, gait, sleep, impedances, evoked compound action potentials (ECAPs), heart rate, heart rate variability, respiration, respiration rate, respiration rate variability or oxygen level.

In Example 8, the subject matter of any one or more of Examples 1-7 may optionally be configured such that the processing system is configured to detect when the patient is sleeping and switch to a sleep program when the patient is sleeping, wherein the sleep program is configured for use to deliver neuromodulation during sleep. The sleep program may be optimized or otherwise specially configured for delivering neuromodulation during sleep.

In Example 9, the subject matter of any one or more of Examples 1-8 may optionally be configured such that the processing system is configured to analyze impedances and/or ECAPs to determine that a change in variability in the impedances and/or ECAPs is indicative of activity, motion and/or posture by determining that the change is in excess of a variability threshold for longer than a duration tolerance.

In Example 10, the subject matter of any one or more of Examples 1-9 may optionally be configured such that the processing system is configured to execute a threshold mapping for different patient postures and/or different patient activities, where the threshold mapping includes determining a perception threshold, a neural threshold or a baseline pain for the different patient postures and/or the different patient activities, and wherein the process for switching to the other program includes determining a patient posture and/or a patient activity and selecting the other program based on the threshold mapping. The neural threshold may include, but not be limited to, thresholds for ECAP or EMG signals, or changing galvanic response. The perception threshold may include, but not limited to, thresholds for paresthesia or vibration.

In Example 11, the subject matter of claim 10 may optionally be configured such that the threshold mapping that is executed by the processing system may include: receiving an assessment trigger; interacting with a user via a user interface for the user to answer questions regarding a specific activity and a duration and level of pain; delivering the neuromodulation at an amplitude, and increasing the amplitude until a signal is received, the signal being indicative that the amplitude of the neuromodulation reached the threshold; providing calibration data by receiving user input indicative of coverage for the neuromodulation and pain relief after the amplitude of the neuromodulation reaches the threshold, the calibration data further including the specific activity and a duration and level of pain before the amplitude of the neuromodulation reaches the threshold; and mapping the analyzed activity, motion and/or posture to at least one of the programs based on the calibration data, wherein the performing the process includes selecting the other program based on the mapping of the analyzed activity, motion and/or posture to the at least one of the programs. The assessment signal may be a signal from an external device such as a remote control, a phone, or a watch, or may be a signal from an internal device. The assessment signal may be indicative a time. The amplitude may be increased until a user input or command is received, such as an input that paresthesia has been felt or until a physiological signal (e.g., an electrophysiological signal such as nerve sensing or ECAP) is detected. The user input indicative of coverage may be provided by rep of the neuromodulation system or a clinician. Both the initial data taken from the questionnaire, before amplitude is stepped up to find the threshold, and the received user input regarding the coverage and pain relief upon reaching the threshold may be used to map the data.

In Example 12, the subject matter of any one or more of Examples 10-11 may optionally be configured such that the set of more than one program includes a base program, and wherein the processing system is configured to automatically generate a plurality of programs around the base program, wherein the plurality of programs are configured to provide modulation field loci at determined distances from a modulation field locus of the base program, wherein the determined distances are determined using field evidence or determined stochastically through a mathematical deterministic or random process, wherein the threshold mapping executed by the processing system includes executing the threshold mapping for each of the plurality of programs that was automatically generated. By way of example and not limitation, the plurality of programs may be automatically generated using a scripting system. Further, by way of example and not limitation, the determined distances may be stochastically determined using a Gaussian or Poisson distributions.

In Example 13, the subject matter of any one or more of Examples 1-12 may optionally be configured such that the analyzed activity, motion and/or posture corresponds to predicted pain, and the processing system is configured to provide closed loop control to adjust the therapy for the predicted pain.

In Example 14, the subject matter of any one or more of Examples 1-13 may optionally be configured such that the processing system is configured to control the neuromodulator to deliver a charge-balanced, active recharge waveform with an actively-driven recharge phase to provide a bolus of increased neuromodulation therapy based on the analyzed activity, motion and/or posture.

In Example 15, the subject matter of any one or more of Examples 1-14 may optionally be configured such that the processing system is configured to receive at least one signal from at least one of a transponder or a GPS system indicative of a patient location, and select the other program based on whether the signal is received. By way of example and not limitation, the transponder signal may indicate that the patient is in a location such as in a particular room, a bed, a chair, a sofa, a room or a car. The GPS system may be a GPS system on a smartphone.

Example 16 includes subject matter (such as a method, means for performing acts, machine readable medium including instructions that when performed by a machine cause the machine to performs acts, or an apparatus to perform). The subject matter may be performed using a neuromodulator programmed with a set of more than one program to deliver neuromodulation. The subject matter may include: implementing a program from the set of more than one program to deliver neuromodulation; receiving sensed data indicative of activity, motion and/or posture of a patient; analyzing the activity, motion and/or posture of a patient from the sensed data; and performing a process, based on the analyzed activity, motion and/or posture, for switching to another program from the set of more than one program, wherein performing the process includes automatically implementing the other program from the set of more than one program or suggesting to switch to the other program from the set of more than one program. The delivered neuromodulation may include SCS therapy. Activity, motion and/or posture may include; activity, motion, posture, activity and motion, activity and posture, motion and posture, or activity, motion and posture. Activity may include predefined activities such as running, walking, standing, sitting, lying down, sleeping, eating. Motion may include movement such as changing postures (sitting to standing, standing to sitting, bending over, twisting trunk, stretching, lying down to sitting, and the like). Posture may include posture states such as sitting, lying down, standing and the like.

In Example 17, the subject matter of Example 16 may optionally be configured to include using a watch or a phone to determine the activity, motion and/or posture.

In Example 18, the subject matter of any one or more of Examples 16-17 may optionally be configured such that the process may include inferring activity and/or posture, the inferred activity and/or posture being indicative of predicted pain, and the process is performed to switch to the other program to alleviate the predicted pain.

In Example 19, the subject matter of any one or more of Examples 16-18 may optionally be configured such that the neuromodulator is configured to deliver neuromodulation using electrodes on a lead. The analyzing activity, motion and/or posture may include detecting activity, motion and/or posture using an accelerometer or gyroscope inside of a tip of the lead.

In Example 20, the subject matter of any one or more of Examples 16-19 may optionally be configured such that the analyzing activity, motion and/or posture includes detecting activity, motion and/or posture using a strain or flex sensor in an implanted lead to detect lead curvature, wherein the implanted lead is implanted along a spine such that the lead curvature is indicative of spin curvature.

In Example 21, the subject matter of any one or more of Examples 16-20 may optionally be configured such that the strain or flex sensor includes a fiber optic bending sensor.

In Example 22, the subject matter of any one or more of Examples 16-21 may optionally be configured such that the analyzing activity, motion and/or posture includes analyzing at least one of posture, gait, sleep, impedances, evoked compound action potentials (ECAPs), heart rate, heart rate variability, respiration, respiration rate, respiration rate variability or oxygen level.

In Example 23, the subject matter of any one or more of Examples 16-22 may optionally be configured such that the analyzing activity, motion and/or posture includes detecting when the patient is sleeping, and the performing the process includes switching to a sleep program when the patient is sleeping. The sleep program may be configured to be used to deliver neuromodulation during sleep. For example, the therapy may be optimized to be conducive for sleep or to promote sleep.

In Example 24, the subject matter of any one or more of Examples 16-23 may optionally be configured such that the analyzing activity, motion and/or posture includes analyzing impedances and/or ECAPs to determine that a change in variability in the impedances and/or ECAPs is indicative of activity, motion and/or posture by determining that the change is in excess of a variability threshold for longer than a duration tolerance.

In Example 25, the subject matter of any one or more of Examples 16-24 may optionally be configured to further include executing a threshold mapping for different patient postures and/or different patient activities. The process for switching to the other program may include determining a patient posture and/or a patient activity and selecting the other program based on the threshold mapping.

In Example 26, the subject matter of any one or more of Examples 16-24 may optionally be configured such that the executing the threshold mapping includes determining a perception threshold, a neural threshold, or a baseline pain for the different patient postures and/or the different patient activities. The neural threshold may include, but not be limited to, thresholds for ECAP or EMG signals, or changing galvanic response. The perception threshold may include, but not limited to, thresholds for paresthesia or vibration.

In Example 27, the subject matter of any one or more of Example 26 may optionally be configured such that the executing the threshold mapping includes: receiving an assessment trigger; delivering the neuromodulation at an amplitude, and increasing the amplitude until a signal is received, the signal being indicative that the amplitude of the neuromodulation reached the threshold; providing calibration data by receiving user input indicative of coverage for the neuromodulation and pain relief; and mapping the analyzed activity, motion and/or posture to at least one of the programs based on the calibration data, wherein the performing the process includes selecting the other program based on the mapping of the analyzed activity, motion and/or posture to the at least one of the programs. The assessment signal may be a signal from an external device such as a remote control, a phone, or a watch, a signal from an internal device. The assessment signal may be indicative a time. The amplitude may be increased until a user input or command is received, such as an input that paresthesia has been felt or until a physiological signal (e.g., an electrophysiological signal such as nerve sensing or ECAP) is detected. The user input indicative of coverage may be provided by rep of the neuromodulation system or a clinician. Both the initial data taken from the questionnaire, before amplitude is stepped up to find the threshold, and the received user input regarding the coverage and pain relief upon reaching the threshold may be used to map the data.

In Example 28, the subject matter of any one or more of Example 27 may optionally be configured such that the executing the threshold mapping includes, before increasing the amplitude, interacting with a user via a user interface for the user to answer questions regarding specific activity, duration and level of pain; and the providing the calibration data includes data indicative of a specific activity, and a duration and level of pain.

In Example 29, the subject matter of any one or more of Examples 26-28 may optionally be configured such that the set of more than one program includes a base program, and configured to further include automatically generating a plurality of programs around the base program, wherein the executing the threshold mapping includes executing the threshold mapping for each of the plurality of programs that was automatically generated. By way of example and not limitation, the plurality of programs may be automatically generated using a scripting system.

In Example 30, the subject matter of any one or more of Example 29 may optionally be configured such that the automatically generating the plurality of programs includes moving neuromodulation field distances determined using field evidence or determined stochastically through a mathematical deterministic or random process. By way of example and not limitation, the determined distances may be stochastically determined using a Gaussian or Poisson distributions.

In Example 31, the subject matter of any one or more of Examples 16-30 may optionally be configured such that the analyzed activity, motion and/or posture corresponds to predicted pain, the method further comprising providing closed loop control to adjust the therapy for the predicted pain.

In Example 32, the subject matter of any one or more of Examples 16-31 may optionally be configured to further include providing a bolus of increased neuromodulation therapy based on the analyzed activity, motion and/or posture.

In Example 33, the subject matter of any one or more of Example 32 may optionally be configured such that the providing the bolus of increased neuromodulation therapy includes delivering a charge-balanced, active recharge waveform with an actively-driven recharge phase.

In Example 34, the subject matter of any one or more of Examples 16-33 may optionally be configured to further include receiving at least one signal from at least one of a transponder or a GPS system indicative of a patient location, wherein the other program is selected based on whether the signal indicative of the patient location is received. By way of example and not limitation, the transponder signal may indicate that the patient is in a location such as in a particular room, a bed, a chair, a sofa, a room or a car. The GPS system may be a GPS system on a smartphone.

Example 35 includes subject matter (such as a device, apparatus, or machine) that may include non-transitory machine-readable medium including instructions, which when executed by a machine, cause the machine to perform a method comprising instructing a neuromodulator to implement a program from a set of more than one program to deliver neuromodulation, wherein the set of more than one program is programmed in the neuromodulator; receiving sensed data indicative of activity, motion and/or posture of a patient; analyzing the activity, motion and/or posture of a patient from the sensed data; and performing a process, based on the analyzed activity, motion and/or posture, for switching to another program from the set of more than one program, wherein performing the process includes automatically implementing the other program from the set of more than one program or suggesting to switch to the other program from the set of more than one program.

An example (e.g., "Example 36") of a system may include a lead with an integrated accelerometer or gyroscope fitted inside a tip or a body of the lead.

An example (e.g., "Example 37") of a system may include a lead with an integrated strain or flex sensor.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figures 1, 2:
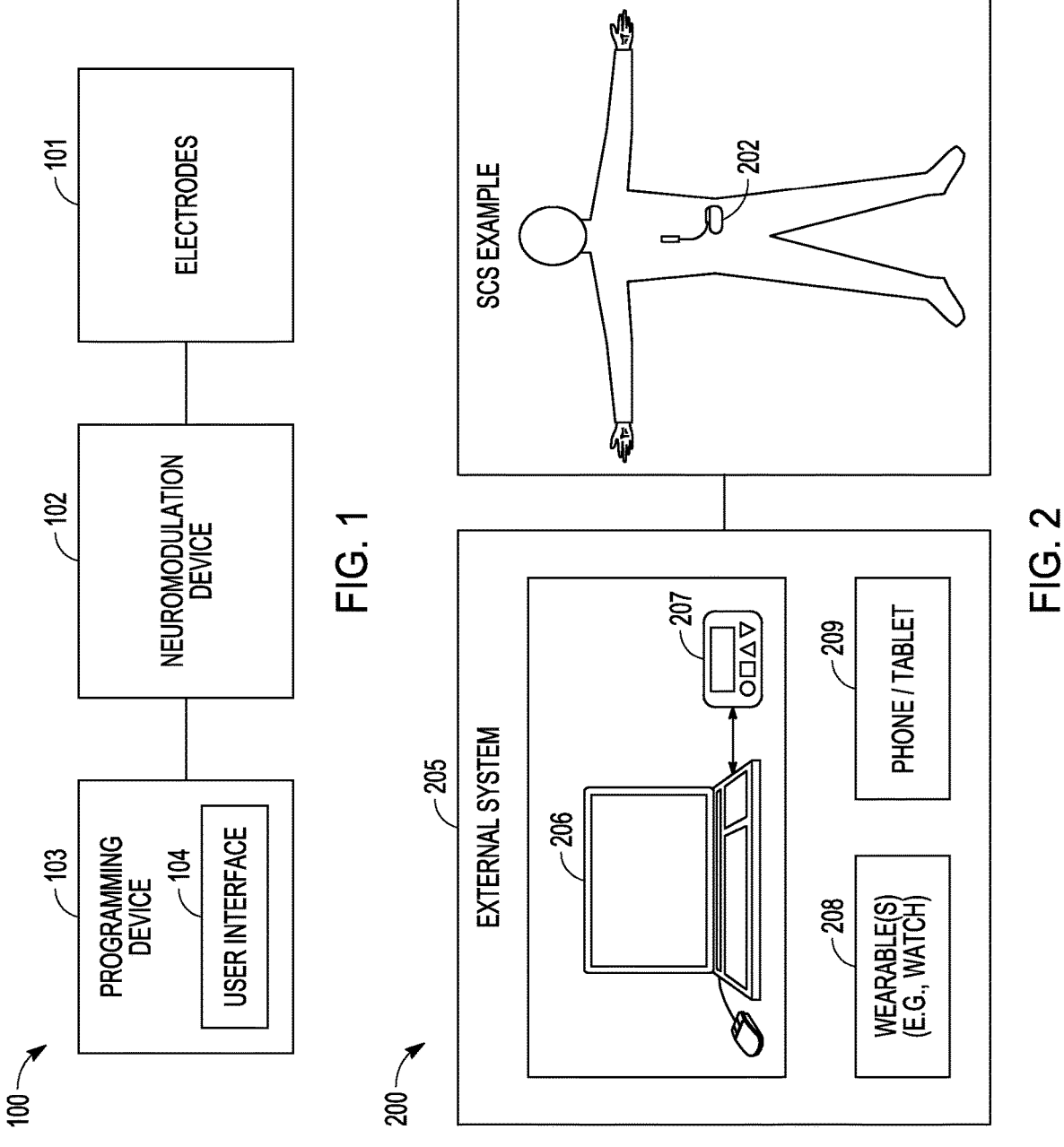
FIG. 1 illustrates, by way of example, an embodiment of a neuromodulation system.
FIG. 2 illustrates, by way of example and not limitation, the neuromodulation system of FIG. 1 implemented in a spinal cord stimulation (SCS) system.

FIG. 1 illustrates, by way of example, an embodiment of a neuromodulation system. The illustrated neuromodulation system 100 includes electrodes 101, a neuromodulation device 102 and a programming system such as a programming device 103, which may be a clinician programmer. The programming system may include multiple devices that may be configured to communicate with each other (e.g., remote control, clinician programmer, and mobile electronic devices such as a phone, tablet, pad and the like). The electrodes 101 are configured to be placed on or near one or more neural targets in a patient. The neuromodulation device 102 is configured to be electrically connected to electrodes 101 and deliver neuromodulation energy, such as in the form of electrical pulses, to the one or more neural targets though electrodes 101. The system may also include sensing circuitry to sense a physiological signal, which may but does not necessarily form a part of neuromodulation device 102. The delivery of the neuromodulation is controlled using a plurality of modulation parameters that may specify the electrical waveform (e.g., pulses or pulse patterns or other waveform shapes) and a selection of electrodes through which the electrical waveform is delivered. In various embodiments, at least some parameters of the plurality of modulation parameters are programmable by a user, such as a physician or other caregiver. The programming device 103 enables the user to access the user-programmable parameters, and may also provide the user with data indicative of the sensed physiological signal or feature(s) of the sensed physiological signal. In various embodiments, the programming device 103 is configured to be communicatively coupled to modulation device via a wired or wireless link. In various embodiments, the programming device 103 includes a user interface 104 such as a graphical user interface (GUI) that allows the user to set and/or adjust values of the user-programmable modulation parameters. The user interface 104 may also allow the user to view the data indicative of the sensed physiological signal or feature(s) of the sensed physiological signal and may allow the user to interact with that data. The neuromodulation device 102, the programming device 103 and other devices or system may collect data that may be used by the neuromodulation system 100. For example, the user interface 104 may be used to allow the user to answer healthcare-related questions.

FIG. 2 illustrates, by way of example and not limitation, the neuromodulation system of FIG. 1 implemented in a spinal cord stimulation (SCS) system. The illustrated neuromodulation system 200 includes an external system 205 that may include at least one programming device. The illustrated external system 205 may include a clinician programmer 206 configured for use by a clinician to communicate with and program the neuromodulator, and a remote control device 207 configured for use by the patient to communicate with and program the neuromodulator. For example, the remote control device 207 may allow the patient to turn a therapy on and off and/or may allow the patient to adjust patient-programmable parameter(s) of the plurality of modulation parameters. FIG. 2 illustrates a neuromodulation device 202 as an implantable device, although a neuromodulation device 202 may be an external device such as a wearable device. The external system 205 may include a network of computers, including computer(s) remotely located from the neuromodulation device 202 that are capable of communicating via one or more communication networks with the programmer 206 and/or the remote control device 207. The remotely located computer(s) and the neuromodulation device 202 may be configured to communicate with each other via another external device such as the programmer 206 or the remote control device 207. The remote control device 207 and/or the programmer 206 may allow a user (e.g., patient and/or clinician or rep) to answer questions as part of a data collection process. The external system 205 may include a wearables such as a watch, sensors or therapy-applying devices. The watch may include sensor(s), such as sensor(s) for detecting activity, motion and/or posture. Other wearable sensor(s) may be configured for use to detect activity, motion and/or posture of the patient. The external system 205 may include, but is not limited to, a phone and/or a tablet.

Figure 3:
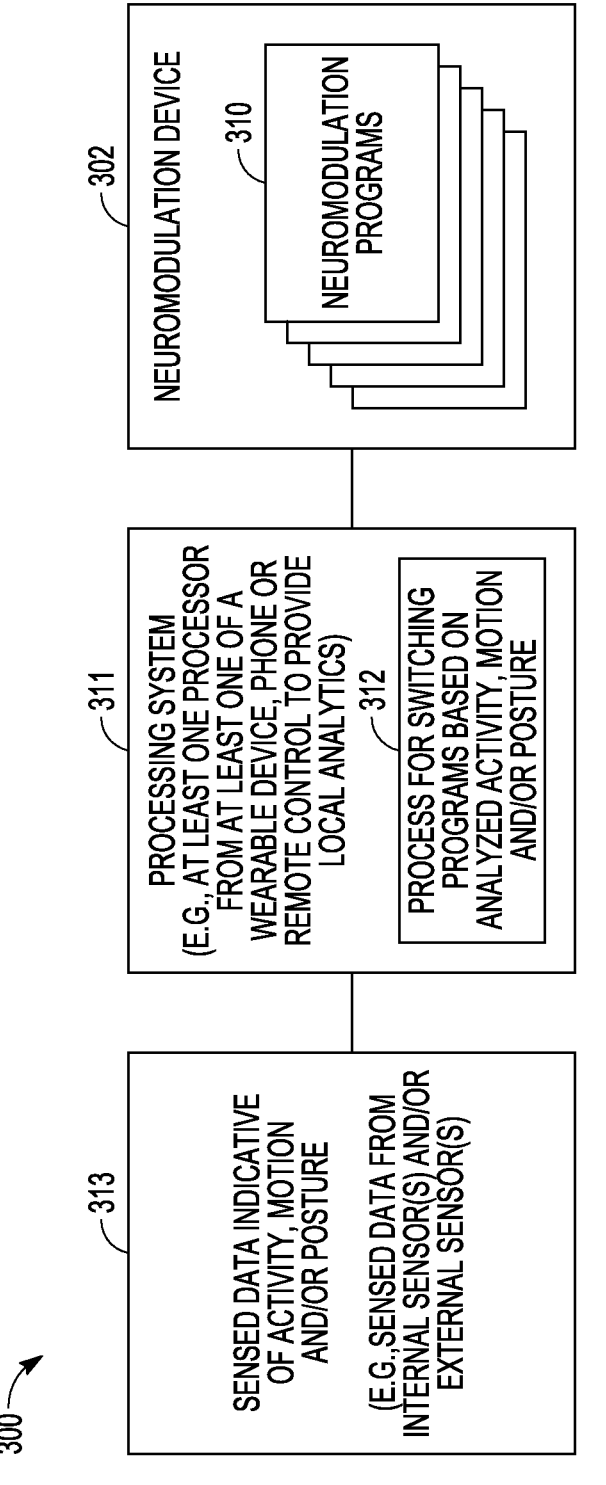
FIG. 3 illustrates, by way of example and not limitation, a neuromodulation system having a neuromodulator programmed with a set of more than one program and a processing system configured to automatically implement another program from the set of more than one program or suggest to switch to the other program based on activity, motion and/or posture.

FIG. 3 illustrates, by way of example and not limitation, a neuromodulation system 300 having a neuromodulation device 302 programmed with a set of more than one program 310 and a processing system 311 configured for performing a process 312 used to switch programs based on activity, motion and/or posture. Each program may define a set of programming parameter values to control the delivery of the neuromodulation energy. Electrical modulation energy is provided to the electrodes in accordance with values for a set of modulation parameters programmed into the waveform generator, and a microcontroller may be used to execute the program to direct and control the neuromodulation performed by the waveform generator. By way of example but not limitation, the electrical modulation energy may be in the form of a pulsed electrical waveform. The pulses may be a regular pulse pattern with consistent pulse widths, amplitudes, and pulse-to-pulse durations. The pulse pattern may include regular bursts of pulses with regular burst-to-burst intervals. The pulse pattern may include irregular patterns of pulses, with variations in the amplitude of pulses, pulses widths, pulse-to-pulse durations, etc. Such variations may be determined according to a function, or may be random or pseudo random. The electrical modulation energy may be delivered using shapes other than pulse shapes defined by a pulse width and pulse amplitude. Modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). Electrodes that are selected to transmit or receive electrical energy are referred to herein as "activated," while electrodes that are not selected to transmit or receive electrical energy are referred to herein as "non-activated." Electrical modulation occurs between or among a plurality of activated electrodes, one of which may be the case of the waveform generator. The system may be capable of transmitting modulation energy to the tissue in a monopolar or multipolar (e.g., bipolar, tripolar, etc.) fashion. Monopolar modulation occurs when a selected one of the lead electrodes is activated along with the case of the waveform generator, so that modulation energy is transmitted between the selected electrode and case. Any of the electrodes one lead(s) and the case electrode(s) may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The waveform generator may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia). The waveform generator may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices. Calibration techniques are used to determine the proper current fractionalization. With the current fractionalized to a plurality of electrodes on the electrical modulation lead, the resulting field can be calculated by superimposing the fields generated by the current delivered to each electrode. The process performed the processing system to switch programs may, based on activity, motion and/or posture, automatically switch programs from the set of more than one program 310 or may suggest to switch programs from the set of more than one program 310. The activity, motion and/or posture may be determined using sensed data indicative of activity, motion and/or posture 313, which may be detected using internal and/or external sensor(s).

Figure 4:
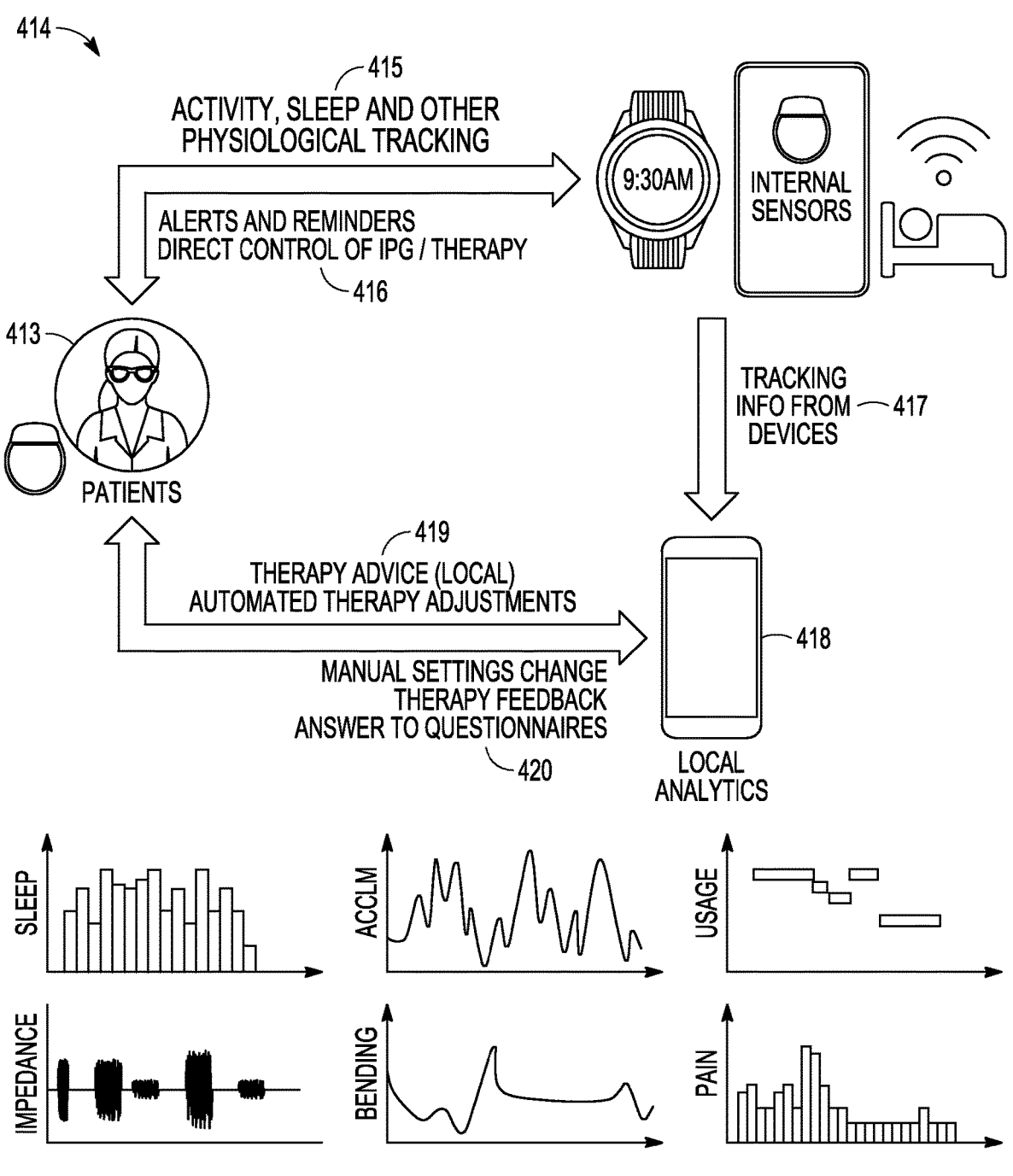
FIG. 4 illustrates, by way of example and not limitation, a neuromodulation system that uses a watch to optimize switching between or among programs based on activity, motion and/or posture.

FIG. 4 illustrates, by way of example and not limitation, a neuromodulation system that determines and analyzes physiological parameters, such as activity, motion and/or posture, for use to switch between or among neuromodulation programs. The system may monitor the patient 413 using tracking devices 414 to determine, as generally illustrated at 415, activity, motion and/or posture or other physiological parameters or states such as sleep. Examples of tracking devices may include a watch with sensor(s), fitness trackers, internal sensors, external sensors, or location sensor(s) such as GPS or transponder(s). A transponder signal may be indicative of a patient location, such as a particular room, a bed, a chair, a sofa, a room or a car. As generally illustrated at 416, at least some of these parameter(s) may be used to provide alerts or reminders to the patient, and at least some of these parameter(s) may be used to direct control of the IPG or the therapy provided by the IPG. At least some of the tracked information 417 from the tracking device, such as activity, motion and/or posture, may be locally analyzed by at least one local device 418 such as a phone, tablet, laptop, or remote control. The analysis may be performed by one local device or distributed among at least two devices. For example, the system may analyze sleep, impedance, acceleration, bending, device usage (e.g., usage of local device or wearable/watch) and pain. The system may analyze gait, ECAPs and the like. The local analytics performed by local device(s) may be used to provide, as generally illustrated at 418, therapy advice (e.g., suggestions for therapy adjustments) or may be used to provide automated therapy adjustment. At least one local device 417 may be used to change manual settings in the neuromodulation device, to provide therapy feedback, and/or answer questionnaires, as generally illustrated at 419.

Some embodiments may execute a perception threshold mapping process for the patient for a variety of postures. For example, a wearable or a remote-control app may be used to execute a perception (pth) or neural (ECAP) threshold (nth) mapping for the patient for a variety of postures and/or activities (sitting, standing, running, working) to get a listing of posture and activities over time and map them to pth and/or nth and coverage. The process may include triggering an assessment based on external or internal signals or based on times. Examples of signals may be from one or more sensors such as an impedance sensor or an accelerometer. The assessment may be triggered by pain. Optionally, a user may be presented with a questionnaire concerning the specific activity, duration and level of pain when the assessment was triggered. The process may further include increasing amplitude until a paresthesia threshold is reached, which may be determined by the user pressing a command button or by detecting an electrophysiological signal such as ECAPs, EMG signals, or a changing galvanic response. The patient, or other user such as a manufacturer rep for the neuromodulator, may provide information about the degree and location of coverage, pain relief and may also provide other information. A set of programs created to deliver neuromodulation near the neuromodulation delivered a base program can also be tested. For example, a patient or other user may be requested to create a new pain drawing to update the coverage information. The correlation between activity and the case-specific calibration provides for an adaptive SCS systems that automatically adjusts therapy based on the patient's needs. Thus, by way of example and not limitation, a base program may be delivered when the patient is at a normal level of activity that corresponds to a first paresthesia threshold, an active program may be delivered when the patient is at a higher level of activity that corresponds to a second paresthesia threshold, and a rest program may be delivered when the patient is sleeping or otherwise resting in bed. Internal and external devices may direct close loop control in a manner that predicts how to adjust therapy according to activity and predicted pain. Various embodiments may detect when a patient is sleeping and provide additional input to optimize therapy during sleep (e.g., activating sleeping programs). Various embodiments may use transponder(s) or GPS systems to alert the SCS system of patient location such as a bed, a sofa or other room. The GPS system may be a GPS system incorporated into a smart phone, for example. Some embodiments integrate location data derived from both the GPS system and the transponder(s) to enable location-specific programs and/or behaviors. Various embodiments may include other physiological sensors such as heart rate, heart rate variability, respiration, respiration rate, respiration rate variability and oxygen levels. Respiration may be monitored using various methods, such as but not limited to transthoracic impedance, which may be used to derive tidal volume and minute ventilation data. Sound may also be used to detect heart rate and respiration data.

Figure 5B:
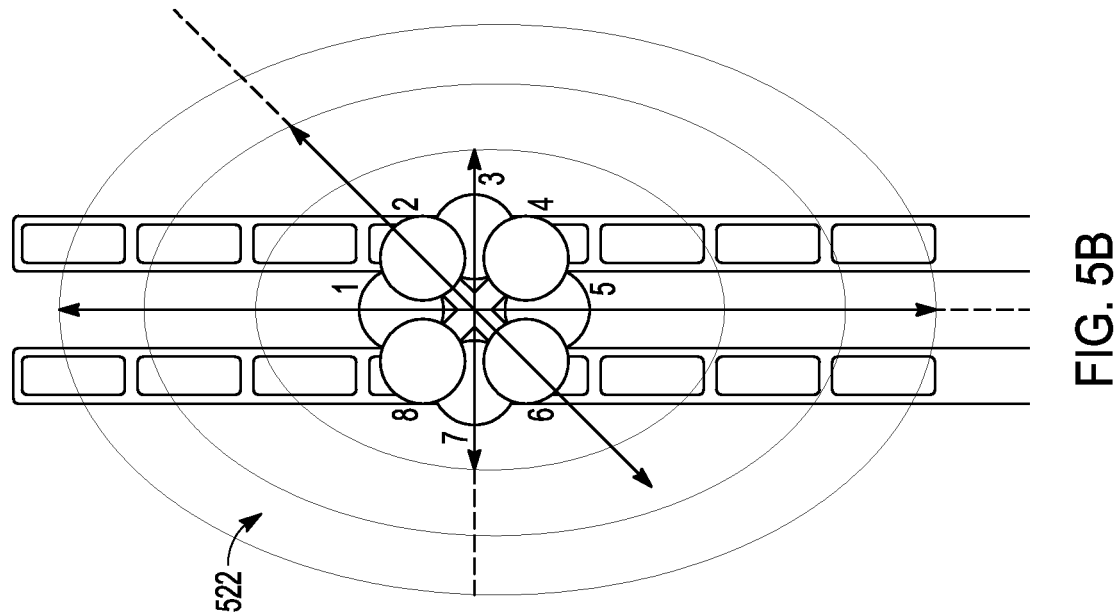
FIGS. 5A-5B illustrates, by way of example and not limitation, the creation of a variety of programs that vary around a base program.
Figure 5A:
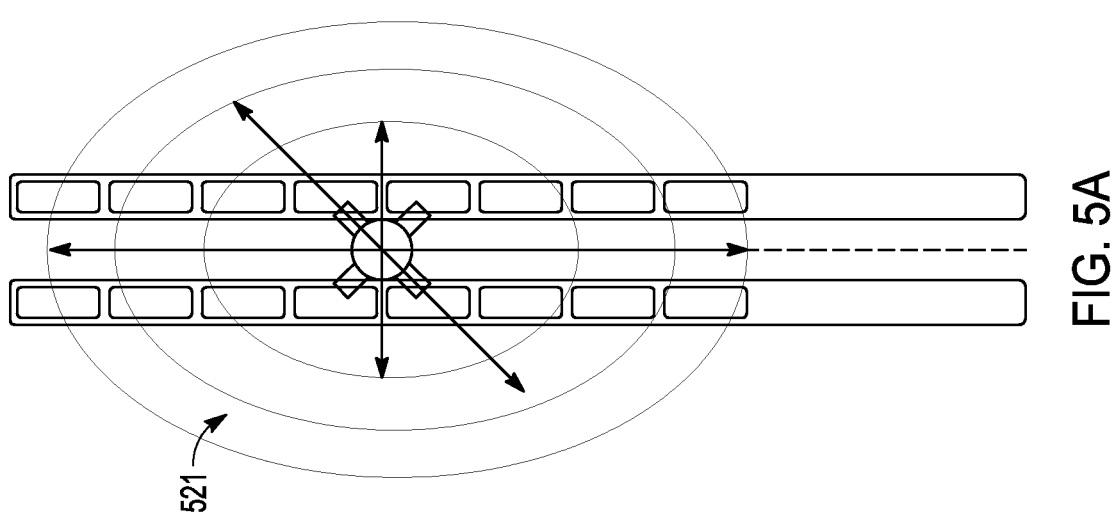

FIGS. 5A-5B illustrates, by way of example and not limitation, the creation of a variety of programs to provide neuromodulation fields 520 that vary around the neuromodulation field 521 provided by a base program. A scripting system may be used to create the programs from the base program, to automatically generate similar programs near neuromodulation field of the base program. These programs may be accessed by the patient at home.

Figure 6:
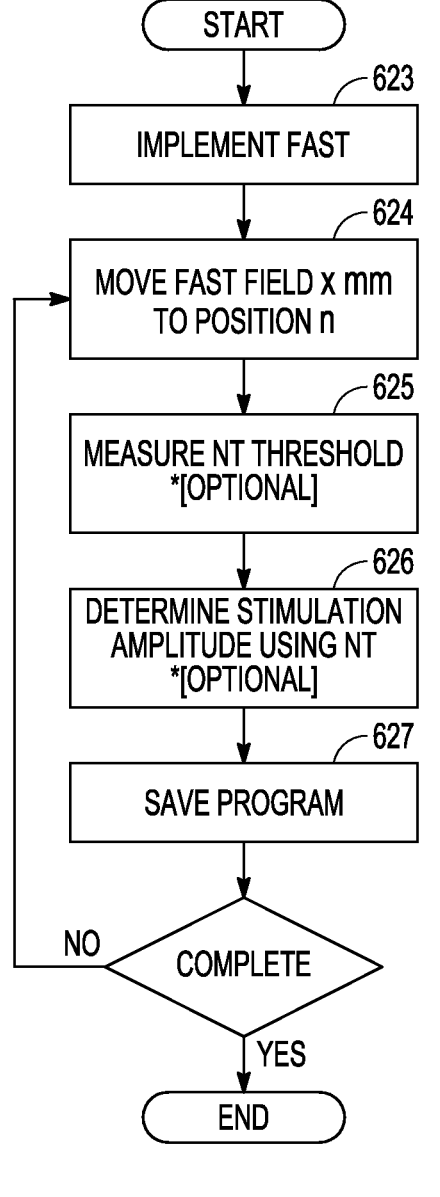
FIG. 6 illustrates, by way of example and not limitation, a method for creating the variety of programs that vary around a base program.

FIG. 6 illustrates, by way of example and not limitation, a method for creating the variety of programs that vary around a base program. The method may use FAST neuromodulation. FAST neuromodulation provides fast-acting subperception therapy for a patient. FAST may include a fitting regime where a patient is tested with supra-perception stimulation (that the patient can feel; that produces paresthesia) to try and find a correct location for stimulation in their electrode array that well "covers" the patient's pain. Finding a correct location for stimulation is typically called "sweet spot searching," because the goal is to find a "sweet spot" in the array for stimulation that well recruits and treats the patient's symptoms, such as lower back pain. Once this "sweet spot" for stimulation in the electrode array is located, the amplitude of the stimulation is lowered to provide sub-perception stimulation (that the patient can't feel), as explained further below.

Both the sweet spot searching the eventually-determined sub-perception stimulation therapy may use a low-frequency (e.g., 90 Hz) active recharge waveform. However, the frequency may be within a range between 1 Hz to 500, a range between 10 Hz and 200 Hz, a range between 50 Hz and 150 Hz, or a range between 80 and 100 Hz. The 90 Hz frequency is a specific example of a desirable parameter value. The pulse width may be 210 us, or within a range between 30 $\mu$s to 500 $\mu$s. The active recharge waveform is biphasic, because it includes two opposite-polarity phases that are both actively driven with constant currents of opposite polarity. Active recharge waveforms recover charge during the second pulse phase (recharge) that was injected during the first pulse phase. Specifically, when current is actively driven during the first pulse phase, charge will be stored on capacitances in the current path. When the polarity and hence direction of the current is reversed during the second phase, such stored charge is actively recovered and pulled off those capacitances. The active recharge waveform used during FAST is symmetric as the amplitude and duration of the two actively-driven pulse phases are the same. However, FAST may be designed to be implemented using asymmetrical pulses.

It is not conventional to use an active recharge waveform at low frequencies in an IPG. Rather, a passive recharge waveform, which includes only a first actively-driven first pulse such as a monophasic, cathodic pulse, is conventionally used as low frequencies. Rather than actively driving a current, passive charge recovery may involve connecting the electrodes to a common voltage causing any stored charge in the current paths to equilibrate by exponential decay through the patient's tissue. Passive recharge is more energy efficient than active recharge since a current is only actively drive during one phase.

A benefit of the active recharge waveform for FAST neuromodulation is that it effectively provides two center points of stimulation using a bipole. A first pole of the bipole may be a cathode pole during the first phase and an anode pole during a second phase, and the second pole of the bipole may be an anode pole during the first phase and a cathode pole during the second phase. These anode and cathode poles need not correspond to the exact positions of the electrodes in the array, but can instead be formed as "virtual poles" between the electrodes.

It is hypothesized that an active recharge waveform affects stimulation at these two CPS locations, which facilitates the identification and optimization of stimulation to patient-specific sweet-spot(s) for pain relief. As a result, when the amplitude of the stimulation is later dropped at this location to sub-perception levels, the source of pain remains well recruited, and provides the patient "FAST" relief from their symptoms. While still providing fast-acting symptomatic relieve, the low-frequency waveforms used in FAST use less power than sub-perception therapy delivered at higher frequencies (e.g., 10 kHz).

By way of example and not limitation, a FAST procedure may include trolling at a low intensity to cover the patient's worst painful area with paresthesia, then turn stimulation down to a percentage (e.g. 70%) of the perception threshold, assess pain including pain while performing an activity (e.g., walking), and if pain reduction is not excellent and very quick (e.g., under 5 minutes), then find a better sweet spot by continuing to troll to cover the painful area and turn stimulation down to the percentage until the pain reduction is excellent and very quick. Once excellent and very quick pain relief is achieved, then the perception threshold may be measured. The sub-perception therapy's maximum amplitude may be set at or otherwise based on the perception threshold. The program may be set to a percentage (e.g., 30%) lower than the perception threshold.

Additional information regarding FAST neuromodulation may be found in the following references, which are herein incorporated by reference in their entirety: U.S. Provisional application Ser. No. 17/347,348, U.S. Pat. No. 10,576,282, US Published App. No. 2020/0009367, 2020/0009394, 2020/0046980, 2020/0147397, 2020/0147390, 2020/0147392, 2020/0147393, 2020/0147388, 2020/0254256, 2020/0147400, and 2020/0147391, and PCT applications WO 2021/003290, WO 2021/0141652 and PCT/US2021/016867.

FAST may be implemented at 623 to provide a base neuromodulation field. Once FAST is implemented the system automatically moves the field to a number of nearby locations (numbered 1-n)×mm away, as illustrated at 624. The distances to the nearby locations may be predefined based on field evidence or may be defined stochastically through a mathematical deterministic or random process (i.e., Gaussian or Poisson distributions, and the like). For each new field location, the perception threshold (PT) may be measured. For each field location the PT can be computed by measuring the Neural Threshold (NT, ECAP threshold) 625. In some embodiments, the NT is used directly instead of PT 625. Optionally, the stimulation amplitude may be determined using the NT 626. The new program may be saved in the IPG 627. These created nearby programs may be available for use by the patient. The patient can activate any one or more of the programs, or the IPG may implement a schedule sequentially activating all the nearby programs.

Figure 7:
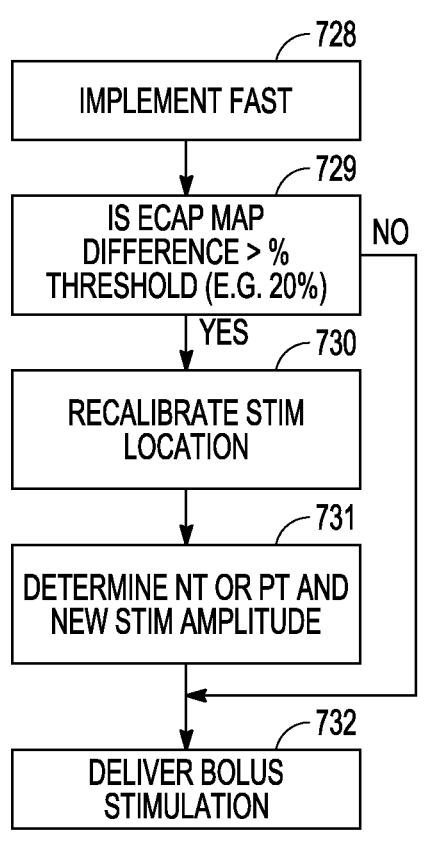
FIG. 7 illustrates, by way of example and not limitation, a method for delivering a bolus neurostimulation.

FIG. 7 illustrates, by way of example and not limitation, a method for delivering a bolus neurostimulation. Various embodiments may provide a "bolus" mode for delivering a bolus of neuromodulation therapy based on activity, motion and/or posture. The bolus mode may be turned on or off by the patient or other user, or by the system. In addition to continuous and cycling modes, patients may benefit from a FAST mode of neuromodulation being delivered "as and when needed" at relatively higher intensity for a shorter amount of time. By way of example, the bolus mode may be particularly beneficial during and right after physical activity, may be particularly beneficial for patients with non-constant pain to use only when needed, and may be particularly beneficial for patients who have previously been running FAST for an extended period of time (e.g., months), and then reporting a reduced need for stimulation.

In an embodiment, an ECAP map may be created at an initial programming visit for the intended FAST program. Just before delivering a bolus mode, a quick lead location check 728 may be performed by measuring the ECAP map. If the two ECAP maps differ by more than a threshold (e.g., differ more than 20%) 729, then the stimulation location may be automatically adjusted and the user may be prompted to recalibrate 730. Otherwise, if the ECAP maps do not differ by the threshold at 729, then the bolus stimulation maybe delivered 732. During recalibration, the user with SW guidance determines the maximum pain paresthesia overlap, using the stimulation parameters previously established for FAST. For the new stimulation location, the NT and/or PT is determined automatically or semi automatically with sweep in amplitude and questions to the subject 731. The bolus stimulation may then be delivered 732.

Figure 8:
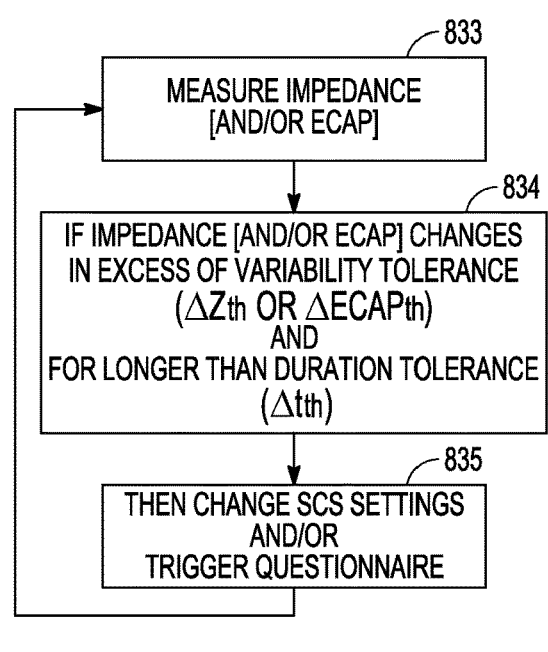
FIG. 8 illustrates, by way of example and not limitation, a method for using variations in a measured parameter (e.g., impedance and/or ECAPs) as an indicator of body motion and physical activity.
Figure 9:
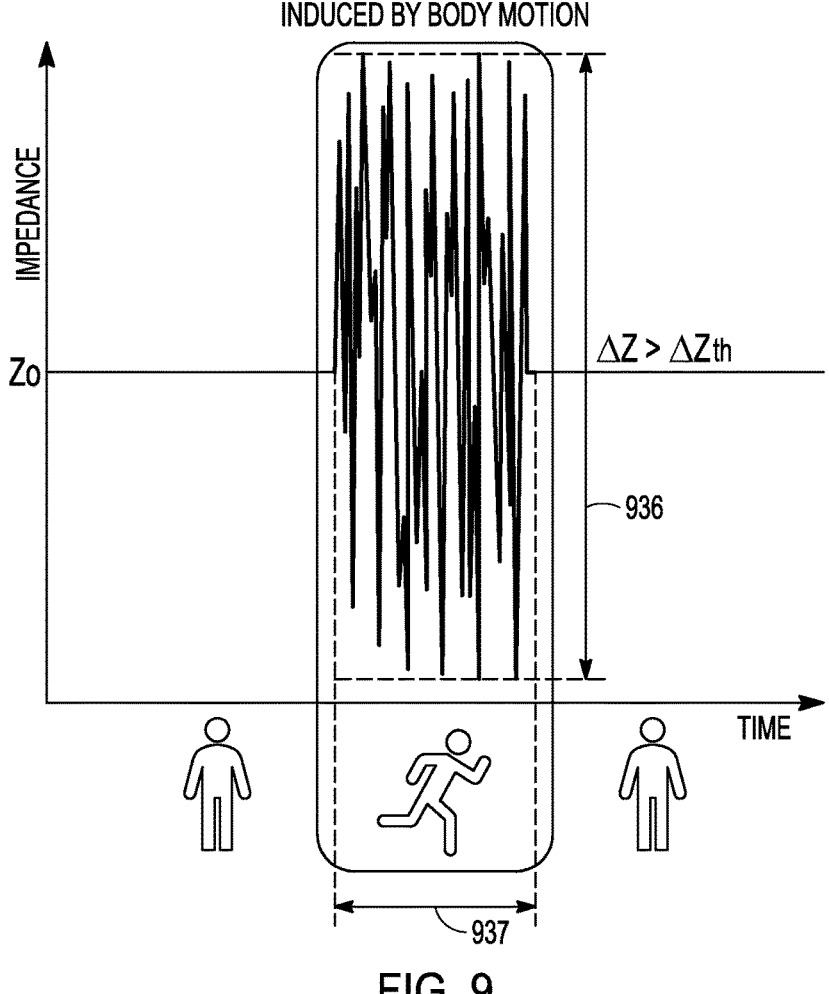
FIG. 9 illustrates, by way of example and not limitation, impedance variability induced by body motion.

FIG. 8 illustrates, by way of example and not limitation, a method for using variations in a measured parameter (e.g., impedance and/or ECAPs) as an indicator of body motion and physical activity. A surge in variability and noise in impedance reading may be used as an indicator of body motion and physical activity. In the illustrated method, impedance and/or ECAPs may be measured at 833. If the impedance and/or ECAP changes exceed a variability tolerance for a time longer than a duration tolerance, as illustrated at 834, then a response is triggered at 835. By way of example and not limitation, the response may include at least one of changing the SCS settings, triggering a questionnaire, performing additional monitoring, or increasing a sampling rate of specific variable(s). The questionnaire may be used by a user (e.g., patient, clinician, rep) to adjust therapy or may be used by an intelligent system (e.g., a system with machine learning) to suggest or adjust the settings. The signal processing may be performed on the implantable neurostimulator, or may be performed on a remote control or an app on a mobile device. The signal processing may be correlated with wearable sensors and data provided by locally administered or cloud questionnaires. The variability may be correlated with other signals, which may be used to change the therapy altogether or just change amplitude. Some embodiments may combine with additional inputs to determine posture and physical activity such as physiological sensed signals (ECAPs, LPFs), accelerometer. FIG. 9 illustrates, by way of example and not limitation, impedance variability induced by body motion. An activity, such as running, may be inferred or otherwise determined if the impedance variability exceeds a threshold ($\Delta Z > \Delta Z_{TH}$) for longer than threshold amount of time ($\Delta T > \Delta T_{TH}$). As illustrated in the figure, the value of the impedance Z varies over a threshold range 936 during a period of time 937.

Figure 10:
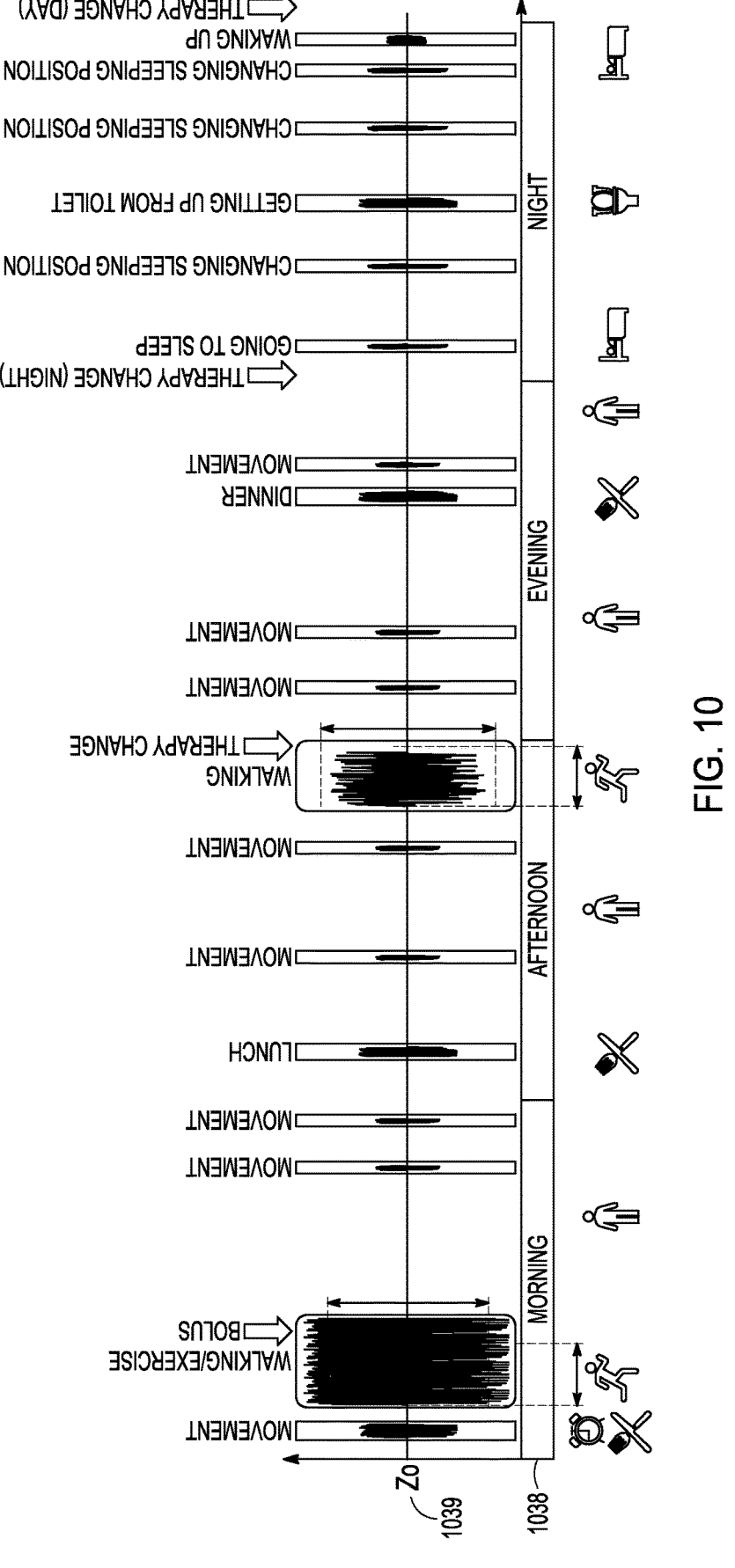
FIG. 10 illustrates, by way of example and not limitation, impedance variability induced by various activities over the course of a day.

FIG. 10 illustrates, by way of example and not limitation, impedance variability induced by various activities over the course of a day. The day is illustrated by a timeline 1038 with labels for Morning, Afternoon, Evening and Night. Above the timeline is an indicator of the variability of impedance (Z) 1039. Specific variability (e.g., a specific range of values over a specific time period) may correspond to various activity, such as waking up and breakfast, walking or exercise, other movements, lunch, walking, dinner, going to sleep, getting up for toilet during the night, and changing sleeping positions during the night. A bolus of therapy may be delivered during the walking/exercise period detected in the morning. Various events may trigger therapy changes. For example, the walking period detected in late afternoon may trigger a therapy change for mild exercise, and going to sleep may trigger another therapy change for patient rest night. The therapy may change again for the day when the patient wakes up again.

Figure 11:
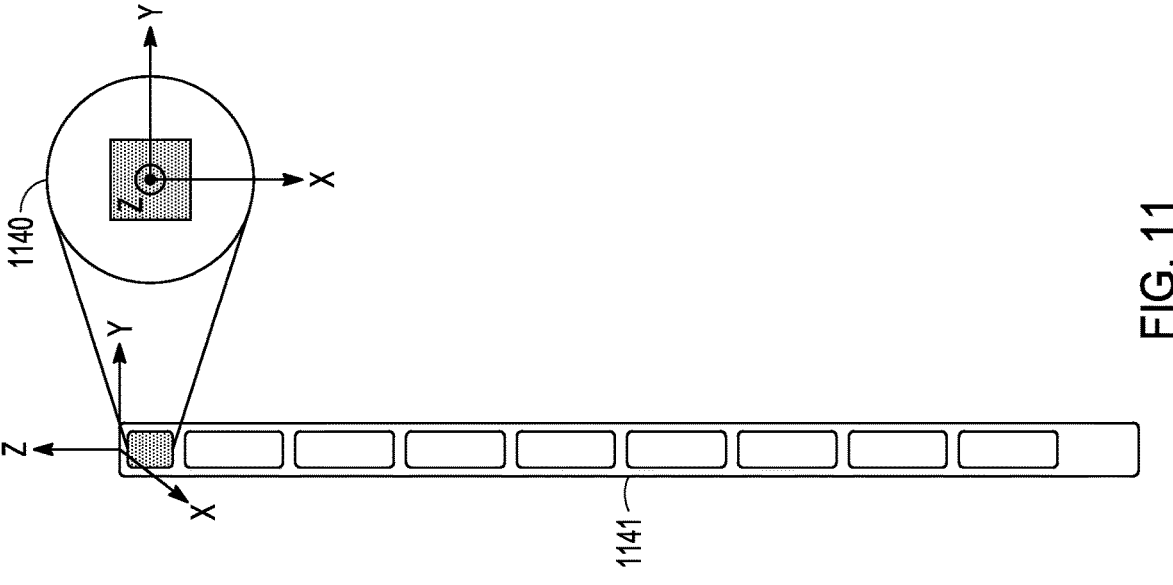
FIG. 11 illustrates, by way of example and not limitation, a miniaturized accelerometer or gyroscope fitted inside a tip or a body of a lead for use to sense movement.

FIG. 11 illustrates, by way of example and not limitation, a miniaturized accelerometer or gyroscope 1139 fitted inside a tip or a body of a lead 1140 for use to sense movement. The lead may include electrodes, wiring electrically connecting the electrodes to a port on a proximal end of the lead, and wiring extending from the accelerometer or gyroscope to the port on the proximal end of the lead. The miniaturized accelerometer or gyroscope fitted inside a tip or a body of a lead may be implemented in an SCS system that is configured to switch programs based on activity, motion or posture. However, the miniaturized accelerometer or gyroscope fitted inside a tip or a body of a lead may be implemented in other SCS systems and in other neuromodulation systems. Furthermore, the miniaturized accelerometer or gyroscope fitted inside a tip or a body of a lead may be implemented in other implantable medical devices such as but not limited to cardiac rhythm management devices (e.g., pacemakers, cardioverters, or defibrillators).

A benefit of the integrated sensor fitted inside a tip or a body of a lead is that it provides information about movement the lead itself rather than movement of the IPG if the sensor in or on the case of the IPG. The movement and/or acceleration of at least one lead may be used to infer activity and/or posture. The illustrated accelerometer or gyroscope may be use alone or in conjunction with other sensos, such as but not limited to impedance sensing, to determine activity, motion and/or posture for the patient, and enabling a system to determine optimal therapy settings. Assessing or predicting patient activity and/or pain may be useful to timely dose a neuromodulation therapy such as a bolus of FAST as well as predict changes in paresthesia.

Figure 12:
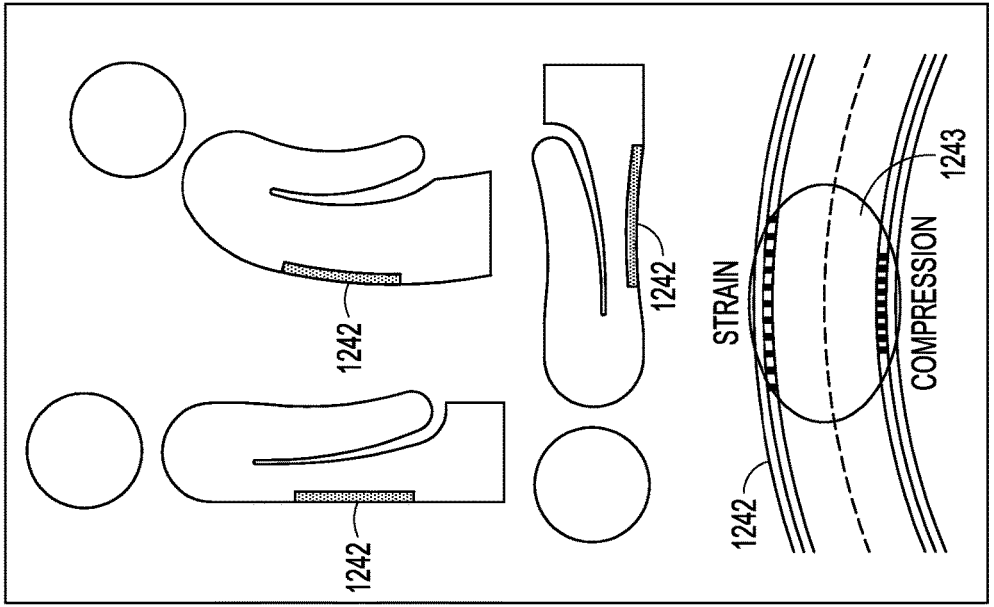
FIG. 12 illustrates, by way of example and not limitation, a strain or flex sensor for use to determine lead curvature indicative of movement or posture.
Figure 12:

FIG. 12 illustrates, by way of example and not limitation, a strain or flex sensor for use to determine lead curvature indicative of movement or posture. The strain or flex sensor may be integrated into a lead to provide information about the lead curvature. The lead with an integrated strain or flex sensor may be implemented in an SCS system that is configured to switch programs based on activity, motion or posture, or may be implemented in other SCS systems and in other neuromodulation systems. Furthermore, lead with an integrated strain or flex sensor may be implemented in other implantable medical devices such as but not limited to cardiac rhythm management devices (e.g., pacemakers, cardioverters, or defibrillators). The sensor may be integrated into the wall of the lead to detect various forces (e.g., tension or compression) or induced flex in the wall of the lead. In the case of an SCS system, the detected lead curvature may reflect spine curvature, which may be used to infer gait and/or postural position. Analysis of curvatures of both lead and spine may be used to infer the relative movement between the spinal cord and the leads/electrodes.

The derived information from the strain or flex sensor may be used to trigger a bolus stimulation or mark changes in paresthesia. The stimulation may be adjusted based on the detected shift between the spinal cord and the leads (or electrodes on the lead). The patient's activity or pain status may be monitored based on information about the posture and gain of the patient. Flex information from the strain or flex sensor may be combined with other sensed data, such as but not limited to impedance, field potential, ECAPs, accelerometer, and the like, to detect changes with more accuracy. This complementary sensing may be desirable as changes in a stimulation field may be related to a relative shift between the spinal cord and the lead. By way of example, a fiber optic bending sensor may be used for sensing, although other sensors may be used such as a piezo-based sensor. A bending sensor may use single piece of regular single-mode fiber or multimode fiber and detect bending by characterizing transmitted intensity as a function of the fiber bending curvature. Fiber optics with fiber Bragg gratings can provide highly sensitive detection of bending/curvature/deformation. Fiber bending sensors may use in-fiber interferometry.

Figure 13A:
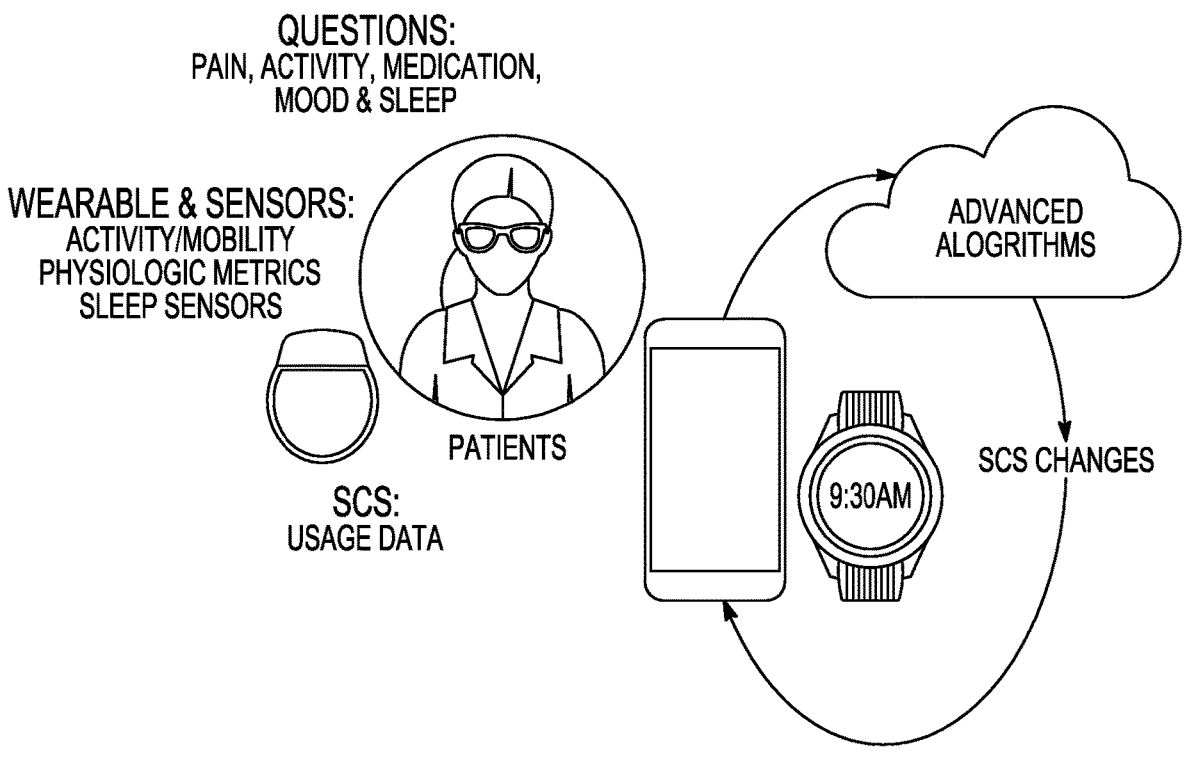
FIGS. 13A-13B illustrate, by way of example and not limitation, some systems with connectivity tools for extending therapy optimization using a phone/remote control app as a bridge for FAST therapy optimization.
Figure 13B:
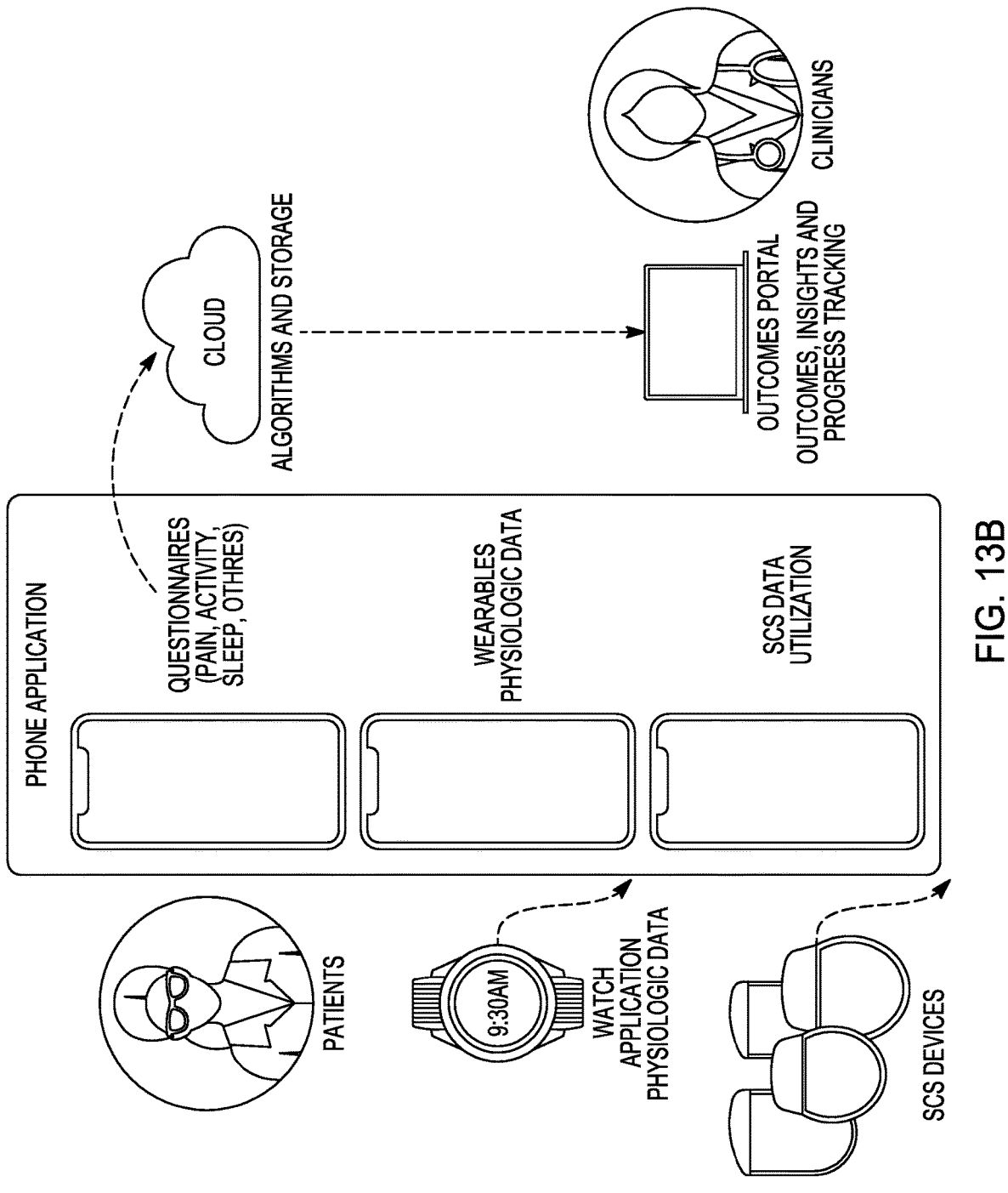

FIGS. 13A-13B illustrate, by way of example and not limitation, some systems with connectivity tools for extending therapy optimization. Existing connectivity tools allow us to further extend those capabilities and use the phone/remote control app as a bridge for FAST therapy optimization. Health-related data for a specific patient may be acquired using questionnaires which may be presented on a device such as a phone, tablet, watch, remote control, or clinical programmer, and various sensors including implantable sensors and external sensors (including wearable sensors such as a watch). The patient heal-related data may also include information from the therapy-providing device (e.g., implantable neuromodulator configured to deliver SCS). The information from the therapy-providing device may include usage data, battery health/life, delivered therapy (e.g., doses of total charge over time), programmed parameters for implemented programs, and the like. Various algorithms may be implemented locally (e.g., FIG. 13A) to determine changes to the therapy (e.g., SCS therapy). The determined changes may be automatically implemented, or may be recommended changes for a user (e.g., clinician, rep or patient) to implement. The system may include a cloud-based system for storing data for the patient and/or for a larger patient population. Algorithms, such as machine learning algorithms, may operate on the collected data to determine changes to the therapy (included automatic changes or suggested changes). The data may be analyzed and presented to clinicians through a portal to allow the clinicians to assess patient outcomes, to gain insights, and track patient progress for the therapy.

Figure 14:
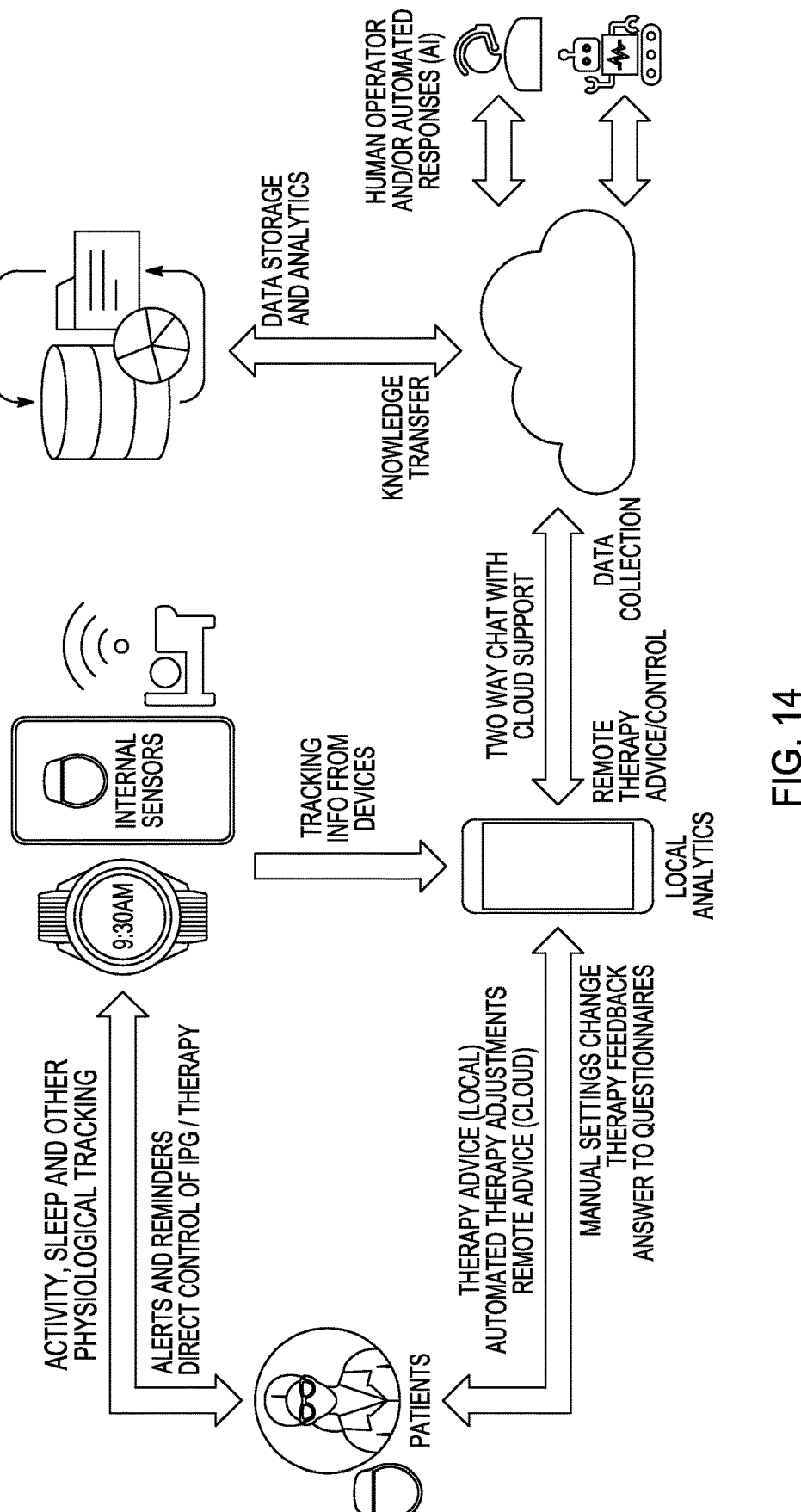
FIG. 14 illustrates, by way of example and not limitation, a system for automatically adjusting programs for users at home using messaging and feedback from the cloud or remote human-based or fully automated programming.

FIG. 14 illustrates, by way of example and not limitation, a system for automatically adjusting programs for users at home using messaging and feedback from the cloud or remote human-based or fully automated programming. The system is similar to the system illustrated in FIG. 4. Additionally, the local device(s) 1417 may be configured to share data, via a cloud-based system 1418, with data storage and analytic system(s) 14445, human operator(s) 1446, and/or artificial intelligence system(s) 1447. The data storage and analytic system(s) may be configured to receive and analyze just the patient data, or may be configured to receive and analyze data from a larger patient population. The analysis may be transferred back to the patient via the local device(s) and/or may be transferred to the cloud support (human operators 1446 and/or AI system(s) 1447). The local device(s) 1417 may receive two-way chat support with cloud support, which may include human operator(s) 1446 and/or AI system(s) 1447. The cloud support may provide therapy advice and/or control back to the patient. This advice and/or control may be based on patient-specific information and/or analytics for that patient, or may be based on information and/or analytics from a larger patient population as well as the patient-specific information and/or analytics. The system may be configured to automatically adjust the programs for users using at home messaging and feedback from the cloud or remote human-based or fully-automated programming.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks or cassettes, removable optical disks (e.g., compact disks and digital video disks), memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A method performed using a neuromodulator programmed with a set of more than one program to deliver neuromodulation, the method comprising:
implementing a program from the set of more than one program to deliver neuromodulation;
receiving sensed data indicative of activity, motion and/or posture of a patient;
analyzing the activity, motion and/or posture of a patient from the sensed data; and
performing a process, based on the analyzed activity, motion and/or posture, for switching to another program from the set of more than one program, wherein performing the process includes automatically implementing the other program to deliver the neuromodulation or suggesting to switch to the other program, wherein:
the set of more than one program includes a base program, and the method further comprises automatically generating a plurality of programs around the base program, the plurality of programs is configured to provide modulation field loci at determined distances from a modulation field locus of the base program, and the determined distances are determined using field evidence or determined stochastically through a mathematical deterministic or random process;
the method further includes, for the base program and each of the plurality of programs that was automatically generated, executing a threshold mapping for different patient postures and/or different patient activities, the threshold mapping includes determining a perception threshold, a neural threshold or a baseline pain for the different patient postures and/or the different patient activities, and
the process for switching to the other program to deliver the neuromodulation includes determining a patient posture and/or a patient activity and selecting the other program based on the threshold mapping.

2. The method of claim 1, further comprising using a watch or a phone to determine the activity, motion and/or posture.

3. The method of claim 1, wherein the process includes inferring activity and/or posture, the inferred activity and/or posture being indicative of predicted pain, and the process is performed to switch to the other program to alleviate the predicted pain.

4. The method of claim 1, wherein the neuromodulator is configured to deliver neuromodulation using electrodes on a lead, and the analyzing activity, motion and/or posture includes detecting activity, motion and/or posture using an accelerometer or gyroscope inside of a tip of the lead.

5. The method of claim 1, wherein the analyzing activity, motion and/or posture includes detecting activity, motion and/or posture using a strain or flex sensor in an implanted lead to detect lead curvature, wherein the implanted lead is implanted along a spine such that the lead curvature is indicative of spine curvature.

6. The method of claim 5, wherein the strain or flex sensor includes a fiber optic bending sensor.

7. The method of claim 1, wherein the analyzing activity, motion and/or posture includes analyzing at least one of posture, gait, sleep, impedances, evoked compound action potentials (ECAPs), heart rate, heart rate variability, respiration, respiration rate, respiration rate variability or oxygen level.

8. The method of claim 1, wherein the analyzing activity, motion and/or posture includes detecting when the patient is sleeping, and the performing the process includes switching to a sleep program when the patient is sleeping, wherein the sleep program is configured to be used to deliver neuro-modulation during sleep.

9. The method of claim 1, wherein the analyzing activity, motion and/or posture includes analyzing impedances and/or ECAPs to determine that a change in variability in the impedances and/or ECAPs is indicative of activity, motion and/or posture by determining that the change is in excess of a variability threshold for longer than a duration tolerance.

10. The method of claim 1, wherein the executing the threshold mapping includes:

receiving an assessment trigger; and responding to the assessment trigger by delivering the neuromodulation at an amplitude, and increasing the amplitude until a signal is received, the signal being indicative that the amplitude of the neuromodulation reached the threshold, providing calibration data by receiving user input indicative of coverage for the neuromodulation and pain relief, and mapping the analyzed activity, motion and/or posture to at least one of the programs based on the calibration data, wherein the performing the process includes selecting the other program based on the mapping of the analyzed activity, motion and/or posture to the at least one of the programs.

11. The method of claim 10, wherein:

the executing the threshold mapping includes, before increasing the amplitude, interacting with a user via a user interface for the user to answer questions regarding specific activity, duration and level of pain; and the providing the calibration data includes data indicative of a specific activity, and a duration and level of pain.

12. The method of claim 1, wherein the analyzed activity, motion and/or posture corresponds to predicted pain, the method further comprising providing closed loop control to adjust the neuromodulation for the predicted pain.

13. The method of claim 1, further comprising providing a bolus of increased neuromodulation therapy based on the analyzed activity, motion and/or posture.

14. The method of claim 13, wherein the providing the bolus of increased neuromodulation therapy includes delivering a charge-balanced, active recharge waveform with an actively-driven recharge phase.

15. The method of claim 1, further comprising receiving at least one signal from at least one of a transponder or a GPS system indicative of a patient location, wherein the other program is selected based on whether the signal indicative of the patient location is received.

16. A non-transitory machine-readable medium including instructions, which when executed by a machine, cause the machine to perform a method comprising:

instructing a neuromodulator to implement a program from a set of more than one program to deliver neuromodulation, wherein the set of more than one program is programmed in the neuromodulator;

receiving sensed data indicative of activity, motion and/or posture of a patient;

analyzing the activity, motion and/or posture of a patient from the sensed data; and performing a process, based on the analyzed activity, motion and/or posture, for switching to another program from the set of more than one program, wherein performing the process includes automatically implementing the other program to deliver the neuromodulation from the set of more than one program or suggesting to switch to the other program to deliver the neuromodulation, wherein:

the set of more than one program includes a base program, and the method further comprises automatically generating a plurality of programs around the base program, the plurality of programs is configured to provide modulation field loci at determined distances from a modulation field locus of the base program, and the determined distances are determined using field evidence or determined stochastically through a mathematical deterministic or random process;

the method further includes, for the base program and each of the plurality of programs that was automatically generated, executing a threshold mapping for different patient postures and/or different patient activities, the threshold mapping includes determining a perception threshold, a neural threshold or a baseline pain for the different patient postures and/or the different patient activities, and the process for switching to the other program to deliver the neuromodulation includes determining a patient posture and/or a patient activity and selecting the other program based on the threshold mapping.

17. The non-transitory machine-readable medium of claim 16, wherein the neuromodulator is configured to deliver neuromodulation using electrodes on a lead, and the analyzing activity, motion and/or posture includes detecting activity, motion and/or posture using an accelerometer or gyroscope inside of a tip of the lead.

18. The non-transitory machine-readable medium of claim 16, wherein the analyzing activity, motion and/or posture includes detecting activity, motion and/or posture using a strain or flex sensor in an implanted lead to detect lead curvature, wherein the implanted lead is implanted along a spine such that the lead curvature is indicative of spine curvature.

19. The non-transitory machine-readable medium of claim 16, wherein the analyzing activity, motion and/or posture includes analyzing at least one of posture, gait, sleep, impedances, evoked compound action potentials (ECAPs), heart rate, heart rate variability, respiration, respiration rate, respiration rate variability or oxygen level.

20. The non-transitory machine-readable medium of claim 16, wherein the analyzing activity, motion and/or posture includes detecting when the patient is sleeping, and the performing the process includes switching to a sleep program when the patient is sleeping, wherein the sleep program is configured to be used to deliver neuromodulation during sleep.

* * * * *